(12) United States Patent
McEwen et al.

(10) Patent No.: US 6,682,547 B2
(45) Date of Patent: Jan. 27, 2004

(54) TOURNIQUET CUFF WITH IDENTIFICATION APPARATUS

(76) Inventors: James Allen McEwen, 10551 Bamberton Drive, Richmond, B.C. (CA), V7A 1K6; Kevin Bryant Inkpen, 1950 Graveley Street, Vancouver, B.C. (CA), V5L 3B4; Michael Jameson, 2365 Badger Rd., North Vancouver, B.C. (CA), V7G 1S9; Kenneth L. Glinz, #20-7651 Francis Rd., Richmond, B.C. (CA), V6Y 1A3

(*) Notice: Subject to any disclaimer, the term of this patent is extended or adjusted under 35 U.S.C. 154(b) by 49 days.

(21) Appl. No.: 09/930,341

(22) Filed: Aug. 14, 2001

(65) Prior Publication Data

US 2003/0036771 A1 Feb. 20, 2003

(51) Int. Cl.$^7$ .............................................. A61B 17/00
(52) U.S. Cl. ..................... 606/202; 606/203; 600/498; 600/499; 356/425
(58) Field of Search ................................ 606/202, 203; 600/498, 499; 602/62, 75; 356/425

(56) References Cited

U.S. PATENT DOCUMENTS

| | | |
|---|---|---|
| 4,469,099 A | 9/1984 | McEwen |
| 4,479,494 A | 10/1984 | McEwen |
| 4,501,280 A * | 2/1985 | Hood, Jr. ..................... 600/490 |
| 4,605,010 A | 8/1986 | McEwen |
| 4,635,635 A | 1/1987 | Robinette-Lehman |
| 4,917,500 A * | 4/1990 | Lugos ......................... 356/406 |
| 4,979,953 A | 12/1990 | Spence |
| 5,022,403 A * | 6/1991 | LaViola ....................... 600/493 |
| 5,048,536 A | 9/1991 | McEwen |
| 5,060,654 A * | 10/1991 | Malkamaki et al. ......... 600/499 |
| 5,150,174 A * | 9/1992 | Ryczek et al. .............. 356/402 |
| 5,181,522 A | 1/1993 | McEwen |
| 5,193,549 A | 3/1993 | Bellin |
| 5,312,431 A | 5/1994 | McEwen |
| 5,411,518 A | 5/1995 | Goldstein |
| 5,413,582 A | 5/1995 | Eaton |
| 5,454,831 A | 10/1995 | McEwen |
| 5,578,055 A | 11/1996 | McEwen |
| 5,584,853 A | 12/1996 | McEwen |
| 5,649,954 A | 7/1997 | McEwen |
| 5,690,672 A * | 11/1997 | Cohen ......................... 606/203 |
| 5,733,304 A | 3/1998 | Spence |
| 5,741,295 A | 4/1998 | McEwen |
| 5,855,589 A | 1/1999 | McEwen |
| 5,911,735 A | 6/1999 | McEwen |
| 5,931,853 A | 8/1999 | McEwen |
| 5,935,146 A | 8/1999 | McEwen |
| 6,124,936 A * | 9/2000 | Okamoto ..................... 356/406 |
| 6,213,939 B1 | 4/2001 | McEwen |
| 6,450,966 B1 * | 9/2002 | Hanna ......................... 600/490 |
| 6,506,206 B1 * | 1/2003 | Guzman et al. ............. 606/203 |

FOREIGN PATENT DOCUMENTS

EP          1016379 A1    12/1999

* cited by examiner

*Primary Examiner*—Eduardo C. Robert
*Assistant Examiner*—David Comstock
(74) *Attorney, Agent, or Firm*—ipsolom llp (57) ABSTRACT

A low cost tourniquet cuff with identification apparatus comprises: an outer strip; an inner strip positioned against the outer strip; a gas-tight seal joining the inner strip to the outer strip to form a cuff having a physical characteristic wherein the cuff includes an inflatable bladder of a predetermined length greater than the circumference of a limb at a selected location; and a cuff connector carried on the cuff and communicating pneumatically with the bladder for releasably connecting to a tourniquet instrument to establish a gas-tight passageway between the bladder and the instrument, wherein the cuff connector includes identification means indicative of the physical characteristic and detectable by the tourniquet instrument upon establishment of the gas-tight passageway. The bladder may be formed by first joining an outer strip having varying thickness to an inner strip along the sides of the outer strip and then further joining the outer and inner strips together with gas-tight seals spaced apart by the predetermined length.

17 Claims, 6 Drawing Sheets

TOURNIQUET CUFF WITH IDENTIFICATION APPARATUS

BACKGROUND

The use of an inflatable cuff to occlude blood flow into a subject's limb, thereby providing a bloodless surgical field in the portion of the limb distal to the cuff over a period of time suitably long for the performance of a surgical procedure, is well known in surgical practice. Tourniquet systems typically include an inflatable cuff for encircling a limb at a selected location and a tourniquet instrument for maintaining the pressure in the cuff near a selected pressure. Such tourniquet instruments of the prior art typically contain, or connect to, a source of pressurized gas and include a pressure regulating mechanism for controlling and maintaining the pressure of the gas supplied to the tourniquet cuff near the selected pressure. Typically a variety of cuff sizes are provided so that a cuff that overlaps itself when encircling the limb may be selected, thereby ensuring that pressure is applied to the limb around its entire circumference. Cuffs are also provided in a variety of shapes, widths, materials, configurations and other physical characteristics as required for different types of patients, limb locations, and surgical procedures.

Some types of tourniquet cuffs of the prior art have relatively complex physical characteristics aimed at safely and effectively occluding blood flow without regard to the cost of manufacture and although relatively effective cannot be manufactured at low cost, especially in small volumes. Other types of prior-art cuffs have simplified physical characteristics that reduce the cost of manufacture but that may not result in the safe and reliable occlusion of blood flow. No low cost, commercially available tourniquet cuff is known in the prior art that allows identification of the type and physical characteristics of the cuff by a tourniquet instrument to which the cuff has been pneumatically connected.

Modern prior art tourniquet instruments employ digital electronic technology in the regulation of pressure and in the detection of certain hazardous conditions. However the selected pressure for the tourniquet cuff is often based on the surgeon's estimate of the minimum pressure required to safely occlude blood flow past the cuff. This minimum safe pressure is affected by the physical characteristics of the cuff, and so providing a convenient and reliable means of identifying certain physical characteristics of the cuff (such as length, width, and type) may be useful for a variety of functions. For example, if a wide cuff is being used, the instrument may display instructions to the surgeon to select a lower tourniquet pressure setting to reduce the chance of pressure related injury while still stopping blood flow effectively. Identification of the cuff also allows optimization of various operation parameters and hazard warning criteria of the tourniquet system. For example if a pediatric cuff is in use, the maximum allowable pressure supplied by the instrument may be reduced accordingly.

If the cuff type can be identified, a record may be kept more easily and more accurately for inventory control and optimization purposes. Such a record may also be used (in combination with recording of other parameters such as pressure used) to aid in establishing safer practice guidelines for the use of surgical tourniquets. Finally, a tourniquet system having automatic cuff identification enables sale or lease of the instrument to a user on a per-use basis or in connection with the purchase of specified quantities of the matching cuffs. A variety of related functions are enabled by an automatic cuff identification feature. For example if an inappropriate cuff is connected, the system may be programmed to warn the user and record the event, but function normally. The cuff identification and recording ability enables the system to be programmed to function with an inappropriate cuff up to a specified number of times only (with associated warnings), then subsequently be disabled unless an appropriate cuff is used.

In many cases, cuffs are color coded to indicate size. For example the 'Comforter™ Disposable Gel Cuff' sold by DePuy Orthopaedics Inc. has a color dot on the outer packaging label corresponding to the cuff size, but no indication of cuff size on the cuff itself. In several other types of tourniquet cuff (for example 'Zimmer ATS Disposable Tourniquet Cuffs', Zimmer Patient Care, Dover, Ohio), components permanently attached to the cuff (such as edge trim and/or tie ribbon) are made of a selected color of material corresponding to the cuff size. These identification means are solely visual and interpretable by the user who is familiar with the color coding scheme. No communication to the instrument is established and therefore no automatic recording, display of information, or adjustment of instrument operating parameters relative to the cuff type can be done.

In U.S. Pat. No. 4,605,010, McEwen describes a tourniquet cuff that includes an electrical means for identifying remotely the physical characteristics of the cuff, as well as for remotely determining the circumference of the limb encircled by the cuff. To permit remote identification of cuff type, the McEwen '010 cuff includes electrically conductive components within the cuff structure, and requires an electrical connection as well as a pneumatic connection between the tourniquet cuff and the tourniquet instrument. Thus electrical power and an electrically conductive pathway are necessarily present within the cuff, in close proximity to the patient's limb encircled by the cuff. This can present a hazard to the patient under some circumstances. Also, inclusion of electrical components within the tourniquet cuff increases the cost and complexity of manufacture of such cuffs. The prior art tourniquet cuff described by McEwen '010 also includes means for allowing a connected tourniquet instrument to remotely determine the circumference of the limb encircled by the cuff. This permits the tourniquet pressure setting to be adjusted, based on the relationship between the physical characteristics of the remotely identified cuff and the remotely identified circumference of the limb encircled by the cuff. No other tourniquet systems in the prior art known to the inventors of the current invention establish a connection other than a pneumatic connection between the cuff and the instrument, such that information about the cuff can be received by the instrument.

Certain tourniquet cuffs of the prior art, known commonly as disposable tourniquet cuffs, are designed and manufactured specifically for use in a sterile surgical field. In many cases such disposable tourniquet cuffs are sterilized after manufacture, are supplied as sterile products, and are discarded after one surgical procedure has been completed. Other tourniquet cuffs of the prior art, known commonly as reusable cuffs, are designed and manufactured for use in multiple surgical procedures. Such prior art reusable cuffs are generally supplied as non-sterile products, and are intended to be thoroughly cleaned and inspected before each surgical procedure. These non-sterile, reusable tourniquet cuffs of the prior art are discarded if inspection before use results in the detection of excessive wear, physical deterioration, or contamination.

The most commonly used cuffs in the prior art typically include three layers of material and a stiffener (Zimmer ATS Disposable Tourniquet Cuffs, Zimmer Patient Care, Dover, Ohio). The inner and outer layers are typically woven nylon coated on one side with thermoplastic polyurethane, the middle layer is plain thermoplastic polyurethane sheet, and the stiffener is made of high density polyethylene sheet. When encircling the patient's limb in use, the inner layer lies against the skin. All three layers are die cut to a particular shape defining the length and width of the cuff, and all have the same perimeter. In a first sub-assembly operation, a port made of thermoplastic material is bonded to the middle layer, creating a gas passageway through the layer that a pneumatic hose may be attached to. In a second sub-assembly operation a reinforcing patch is bonded to the outer layer. In a third sub-assembly operation hook and loop fastening materials are sewn to the outer layer (thus rendering the outer layer gas permeable and therefore unsuitable for forming an inflatable portion of the cuff). The inner layer, middle layer with port, stiffener, and outer layer sub-assembly are then manually loaded into a die, aligned, and a press-type radio frequency (RF) sealing operation used to join the layers in a continuous gas-tight seal around the perimeter of the cuff. This results in a cuff with an inflatable bladder between the inner and middle layers, which can be inflated and deflated via the port, and a stiffener lying in the non-inflating space between the middle and outer layers. With this construction the stiffener is narrower and shorter than the bladder and lies inside the inner perimeter of the bladder-forming seal, so that the seal joins three layers of constant thickness materials around its entire perimeter. To create a smooth, rounded edge along the perimeter of the cuff that will not chafe the patient's skin, an edge trim of nylon ribbon material is folded over the edge of the cuff around the perimeter of the cuff and sewn in place. Finally a nylon tie ribbon is sewn to one end of the cuff and an identifying label is sewn to one end of the hook-type fastening strap.

The tourniquet cuffs known in the prior art as described above have a relatively high cost of manufacture because the manufacturing process is relatively labor intensive. Also, to maintain a consistently high quality of manufactured product and thus reduce the rate of sub-standard products rejected during manufacture, these prior art tourniquet cuffs must be made by staff who have a relatively high level of training, skill and experience. These prior art cuffs are not well suited for a flexible manufacturing process in which different sizes of tourniquet cuffs are manufactured in small batches and rapid changeover from one type of cuff to another is possible. Finally, the maximum length of cuff that can be manufactured is limited by the sizes of the various die cutting and RF sealing equipment available. These limitations of the prior art are described in more detail below.

For each of the three RF sealing stages described above, an operator must load the individual layers of material into an RF sealing die in the correct order, alignment and orientation, activate the RF press for approximately 5 seconds, and then unload the die manually. Improper positioning of any one of the layers or the stiffener (for example if an edge of the stiffener encroaches into the RF sealed area around the perimeter of the cuff) may cause failure of the cuff. Before the final RF seal operation, a skilled operator must sew two separate pieces of hook and loop fastener material to the outer layer sub-assembly. These components must be centered between and parallel to the cuff sides and the stitching must be continuous and accurately positioned (particularly where it passes through the reinforcing patch) or a potentially hazardous structural failure may occur when the cuff is inflated. Because each cuff size and type has a unique perimeter, each requires a unique cutting die and certain unique RF sealing dies, fixtures, and press setups. Cuff length is limited by the table size of the die cutting and RF sealing equipment, and also by the length of RF sealing die that can produce a constant thickness seal along the entire length of the cuff.

After the final RF seal operation, the available width for sewing the tie ribbon and edge trim in place around the cuff perimeter (distance between the outer perimeter of the seal forming the inflatable bladder portion of the cuff and the outermost edge of the cuff material) is typically only 0.38 inches. Sewing the edge trim and tie ribbon in place is therefore particularly labor intensive and skill dependent because any encroachment of the stitching into the inflatable bladder portion of the cuff may cause the cuff to leak or burst when inflated. Conversely if the sewn joint passes outside the cuff material perimeter the edge trim or tie ribbon will not be securely attached in that area. Increasing the 0.38 inch width, thereby increasing the overall cuff width and length for a given inflatable bladder size, presents a safety-related problem because it is well established in the surgical literature that if all other design parameters are the same, the widest possible bladder width within a given overall cuff width will result in the lowest tourniquet pressure being required to stop blood flow past the cuff. Lower cuff pressures are desirable surgically because lower pressures are correlated with lower probabilities of injury to the limb encircled by the cuff. Alternatively stated, it is well established that a reduced bladder width within a given overall cuff width requires the use of higher tourniquet pressures to stop blood flow, and higher pressures are associated with higher probabilities of patient injury.

Tourniquet cuffs described by Guzman in European patent application EP1016379A1 and in commercial products manufactured in accordance with its teachings ('Comforter™ Disposable Gel Cuff', DePuy Orthopaedics Inc) include an inner layer material having a soft, felt-like surface lying against the limb. Along certain edges of the cuff the perimeter of the inner layer extends beyond the perimeter of the remaining layers and is folded over the edges of the remaining layers, thereby creating a rounded edge of soft material along the edges and protecting the patient from chafing. The folded-over edges are held in place by stitching lying outside the perimeter of the seal forming the inflatable bladder portion of the cuff, in a similar fashion to the edge trim attachment method used in the prior art Zimmer cuffs described above. Although the folded over edge arrangement eliminates the separate edge trim component used in the Zimmer cuffs, it suffers from the same disadvantages described in the preceding paragraph concerning labor intensiveness, skill dependency, and overall cuff width for a given bladder width.

In U.S. Pat. No. 4,979,953, Spence describes a tourniquet cuff with an edge trim sewn through the inflatable bladder seal, rather than outside the perimeter of the bladder seal. Although this arrangement may allow a wider bladder for a given overall cuff width and seal width compared to the Zimmer and DePuy cuffs described above, there is even less margin for error in the edge trim installation procedure because the stitching runs even closer to the inner perimeter of the inflatable bladder seal. Using a wider seal to overcome this problem (for example 0.50–1.0 inches as suggested by Spence in the '953 patent) results in a narrower bladder width and correspondingly higher required cuff pressures and risk of pressure-related injury to the patient. Seal widths range from 0.13 inches to 0.25 inches in commercially available tourniquet cuffs known to the inventors of the current invention.

Certain tourniquet cuffs of the prior art do not have edge trim or folded edge as described above. This reduces the cost of cuff manufacture and simplifies the manufacturing process but may introduce a hazard when such a cuff is applied to the limb of a patient. For example in the tourniquet cuff described by Spence in U.S. Pat. No. 5,733,304 and in commercial products manufactured in accordance with its teachings ('Color Cuff II' sterile disposable tourniquet cuffs, InstruMed Inc., Bothell Wash.) the bond between the inner and outer layers extends to the outer perimeter of the cuff, presenting a stiff, sharp edge that could contact the patient's skin and cause injury. Accordingly a separate limb protection means, such as the stockinette sleeve supplied with the 'Color Cuff II', may be necessary to protect the limb from injury near the edge of the cuff and thus assure an adequate level safety for the patient. The need to use a separate limb protection sleeve in conjunction with such prior art cuffs adds an additional cost for the user and offsets the lower cost of cuff manufacture of such cuffs. Similarly the tourniquet cuff described by Robinette-Lehman in U.S. Pat. No. 4,635,635, commercial products manufactured in the past in accordance with its teachings ('Banana Cuff' sterile disposable tourniquet cuffs, Zimmer Arthroscopy Systems, Englewood Colo.), and the tourniquet cuffs described by Eaton in U.S. Pat. No. 5,413,582 do not have edge trim and the sharp edges of the cuff may present a hazard to the patient. In U.S. Pat. No. 5,193,549 Bellin describes a cuff made of a sheet of material folded in half and sealed along the resulting three edges to form a bladder, in which the folded edge is not sharp but the three sealed edges are sharp and do not have an edge trim. In U.S. Pat. No. 5,411,518 Goldstein describes a cuff similar to the Color Cuff II and additionally including a separate border material applied around the perimeter of the cuff and a separate pad to be used with the cuff to protect the patient's skin, thereby suffering from the disadvantages of increased manufacturing complexity and cost as discussed above. No prior art tourniquet cuff is known to the inventors of the current invention in which two strips of material form the inflatable bladder (allowing a low-cost continuous manufacturing process) wherein at least one of the longitudinal edges is further formed into a soft, rounded shape and is held in this shape by the seal forming the inflatable bladder of the cuff, thereby reducing cost by eliminating additional edge trim components and attachment operations.

Tourniquet cuffs of the prior art generally include a thermoplastic port permanently attached to the inflatable bladder allowing attachment of a pneumatic hose for pressurizing the cuff. Prior art ports consist of a planar flange that is RF sealed to the wall of the inflatable bladder and a cylindrical body portion extending out of the bladder in a radial direction away from the limb. A gas passageway passes through both the body and the flange to the bladder. Under certain circumstances the gas passageway may be blocked by the flexible material of the bladder lying against the planar flange, for example if the patient's weight is pressing down on the port. This may lead to a condition in which pressure remains in the cuff after the surgeon has deflated it and the instrument indicates zero pressure, or a condition in which the cuff does not reach full pressure as indicated on the instrument. Both conditions may be hazardous to the patient.

To minimize the chance of pneumatic hoses encroaching on the surgical field distal to the cuff, many prior art ports have a 90 degree bend in the body portion and an extension of the body pointing proximally beyond the perimeter of the flange. Hoses connected to the port will therefore run in a proximal direction (away from the surgical field) and lie flat against the patient's limb. Such ports suffer from the same risk of blockage as described above. In addition they complicate the cuff manufacturing process because the extended portion of the body must be manually passed through the hole in the bladder wall, then turned 90 degrees such that the flange portion lies parallel to the bladder wall. In order to form an uninterrupted gas tight seal between the flange and the outer layer, the RF sealing die must be recessed and the port and bladder wall assembly must be manually passed through the recess before sealing. In all prior art tourniquet cuffs known to the inventors of the current invention, the port flange surface inside the inflatable bladder is substantially planar; none have any provision for preventing blockage by the opposite bladder wall.

Tourniquet cuffs of the prior art generally include a stiffener cut from a sheet of flexible plastic material (such as high density polyethylene) to constrain the inflatable bladder portion of the cuff and thereby direct expansion of the bladder inwardly towards the limb when the cuff is inflated. The stiffener must therefore lie outside the inflatable bladder (for example in a non-inflating sheath as in the Zimmer cuffs described above) or otherwise lie against the outer layer of the bladder when the cuff is inflated. Some tourniquet cuffs in the prior art (Oak Medical, Briggs, North Lincs, UK, and described by Eaton in U.S. Pat. No. 5,413,582) consist of two layers only, wherein the outer layer is a gas impermeable stiffener material of constant thickness and stiffness extending across the entire cuff width. As described by Eaton in the '582 patent, this arrangement can allow a continuous manufacturing process in which the two long strips of material are extruded and joined along the edges, then cut to length and sealed across each cut ends to form an inflatable bladder. However due to the uniform thickness and stiffness of the outer layer, the inner layer must stretch and/or the outer layer edges must curl towards the limb in order for the cuff to expand inwardly toward the limb. Based on testing done by the inventors of the current invention, the stiff proximal and distal edges of such cuffs tend to kink and buckle inwards towards the limb, presenting a potential chafing and pinching hazard to the patient. Furthermore the distribution of pressure actually applied to the limb is more likely to be uneven due to the resulting kinks. Testing done by the inventors of the current invention also shows that substantially higher pressures are required in the Oak Medical cuff to occlude blood flow in a typical limb compared to other prior art cuffs. Thus, Eaton's teachings in the '582 patent and the Oak Medical cuff are examples of prior-art cuffs having simplified physical characteristics that reduce the cost of manufacture but that also reduce the safety and reliability of blood flow occlusion due to the stiff cuff edges. No prior art is known to the inventors of the current invention in which a stiffened portion along the middle of the outer layer (but not extending the full width of the bladder) is continuous along the full length of the cuff and passes through the bladder end seals, thereby allowing a lower cost continuous manufacturing method utilizing a substantially constant cross-section strip to form the outer layer of the cuff.

In certain embodiments of tourniquet cuffs described by Spence in U.S. Pat. No. 5,733,304, in commercial products manufactured in accordance with its teachings ('Color Cuff II' sterile disposable tourniquet cuffs, InstruMed Inc., Bothell Wash.) and certain embodiments of tourniquet cuffs described by Goldstein in U.S. Pat. No. 5,411,518, a stiffener is placed in the inflatable bladder but not secured to the outer layer of the bladder or any other portion of the cuff. With this arrangement the stiffener may lie against the inner or outer layer of the bladder when the cuff is inflated and therefore may not restrict outward expansion of the outer layer. Furthermore the stiffener as shown in the '304 patent and the '518 patent may shift in the bladder and block the gas passageway entering the bladder, preventing proper inflation or deflation of the cuff and thereby posing a hazard to the patient. Note also that in these cuffs the stiffener does not carry any circumferential tensile loads when the cuff is inflated.

Tourniquet cuffs described by Guzman in European patent application EP1016379A1 and commercial products manufactured in accordance with its teachings ('Comforter™ Disposable Gel Cuff', DePuy Orthopaedics Inc) include first and second cavities formed by at least three layers of material. The first cavity lies between the limb and the second cavity, is filled with a gel-like material, and is not pressurized at any time during use of the cuff. The second cavity is an inflatable bladder which is pressurized to occlude blood flow in the limb, as in typical pneumatic tourniquet systems. In the 'Comforter™' cuffs the two cavities have the same perimeter and are formed by a continuous seal joining the three layers of material. The three material layers each have a uniform thickness and stiffness, and there is no stiffener in these cuffs. The purpose of the gel-like material is to more evenly distribute the pressure applied by the cuff to the patient's limb and therefore be more comfortable for the patient. However, adding the gel layer leads to a substantially thicker cuff compared to other prior art cuffs, which may lead to major variations in the pressure applied to the limb in the overlapping region. The inventors of the current invention have tested various prior art cuffs and found that greater cross sectional thickness causes greater pressure discontinuities in the region of the overlap. In particular, the pressure actually applied to the limb in the region of the overlap could be much less than the inflation pressure of the cuff, thus creating low pressure pathways longitudinally through which arterial blood could enter the limb. Furthermore, a thicker cuff leads to a greater difference in circumference between the inner and outer layers when the cuff encircles the limb causing more severe wrinkling of the inner layer as it is forced around a substantially smaller radius than the outer layer. In testing done by the inventors of the current invention, DePuy Gel Cuffs were found to require significantly greater pressures to occlude typical limbs in comparison to other prior art cuffs and were also found to create large pinches and wrinkles in the patient's skin both at the cuff overlap and around the remaining circumference of the limb. The gel material also significantly increases the amount material in the cuff and the cost and complexity of manufacture. Conversely, as found in testing conducted by the inventors of the current invention, thin cuffs tend to apply more even pressure to the limb and tend to wrinkle less along the inner layer when encircling the limb. If desired and if the extra cost is warranted, corresponding pinches and wrinkles in the patient's skin under the cuff may be more effectively prevented by use of a limb protection sleeve specifically designed for use with the cuff as described by McEwen in U.S. patent application Ser. No. 09/378,034 filed Aug. 20, 1999.

Similarly the tourniquet cuff described by Robinette-Lehman in U.S. Pat. No. 4,635,635 and commercial products manufactured in the past in accordance with its teachings ('Banana Cuff' sterile disposable tourniquet cuffs, Zimmer Arthroscopy Systems, Englewood Colo.) are made of five layers of material including bladder inner and outer layers, a separate sheath of reinforced material containing the stiffener, and an additional inner layer. This construction leads to a thick, complex cuff suffering from the disadvantages described in the preceding paragraph.

DETAILED DESCRIPTION OF THE PREFERRED EMBODIMENT

A specific embodiment illustrated is not intended to be exhaustive or to limit the invention to the precise form disclosed. It is chosen and described in order to explain the principles of the invention and its application and practical use, and thereby enable others skilled in the art to utilize the invention.

Throughout this document the terms 'bond' and 'bonded' will generally refer to processes such as radio frequency (RF) welding, ultrasonic sewing and welding, other forms of plastic welding, adhesive bonding, or solvent bonding selected to be suitable for the materials and coatings chosen for the various components of the cuff. Width and thickness of the bonds are selected to produce a joint of sufficient strength to withstand the stresses produced by typical cuff inflation pressures up to 500 mmHg at various limb circumferences, and in selected areas, to form a gas impermeable joint between the materials. The terms 'seal' and 'sealed' refer specifically to gas-tight or gas impermeable joints forming an inflatable bladder.

Figure 1:
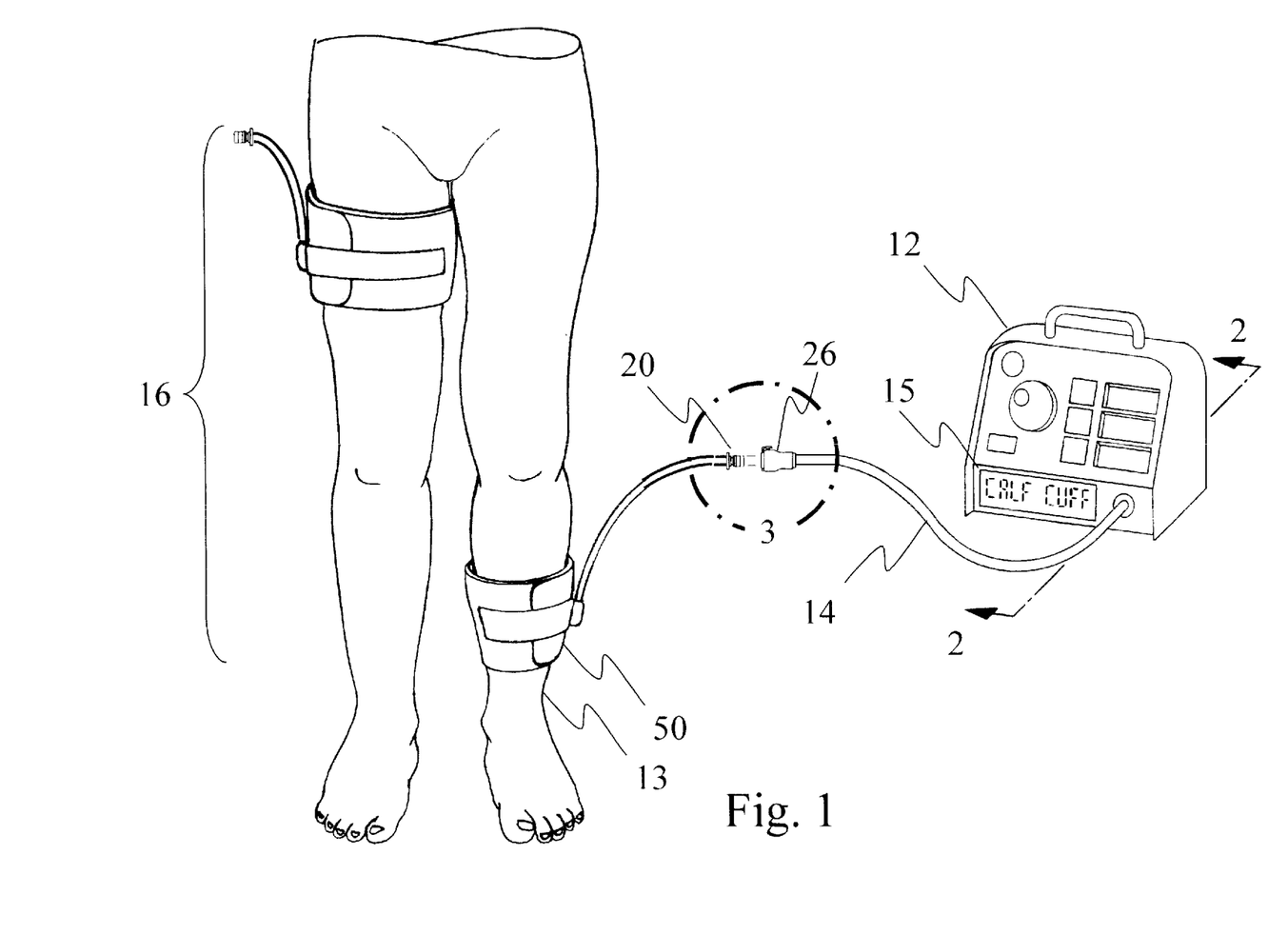
FIG. 1 is shows the tourniquet system with cuff identification means and a set of cuffs.

FIG. 1 shows the preferred embodiment of the invention consisting of tourniquet instrument 12, fill line assembly 14, and cuff set 16. Cuff set 16 comprises cuff 50 which has physical characteristics suitable for application to a lower leg within size and shape limits and cuff 51 which has different physical characteristics suitable for application to a thigh within different size and shape limits. For clarity, physical characteristics of cuff 50 and cuff 51 include their size, shape, materials, and stiffness. Also for clarity, a physical characteristic may be predetermined to allow identification of the manufacturer of cuff 50 and 51 by tourniquet instrument 12 in the same way that a label allows visual identification of the manufacturer. As described below cuff 50 includes an inflatable bladder portion and has a port manifold 76, hose 74, and cuff connector 20 permanently attached allowing a source of pressurized gas to be connected to the bladder. Cuff set 16 may comprise, for example, different size cuffs of similar design, a selection of cuffs designed for use on pediatric patients, or cuffs made by a particular manufacturer and are appropriate for use with the system. Each cuff in cuff set 16 has a distinctly colored cuff connector 20 indicating its distinct physical characteristics both to the user (visually) and to instrument 12 as described below.

When the system is being used in surgery, at least one cuff from cuff set 16 is wrapped around the patient's limb 13 at a location proximal to the surgical site. Cuff 50 from cuff set 16 is shown in FIG. 1 connected to fill line assembly 14 by engaging cuff connector 20 (a suitable connector being a custom tinted version of the DSM2202 connector manufactured by Colder Products Company, St. Paul, Minn.) with fill line connector 26 (a suitable connector being a modified version of a PMC 17-02 female locking connector made by Colder Products Company, St. Paul, Minn.). The embodiment shown is a "single port" system in which fill line assembly 14 provides a single gas-tight passageway from instrument 12 to cuff 50 for the purpose of inflating, sensing and regulating the pressure in, and deflating the cuff as required by the user (as is typical in many modern tourniquet systems). In the current invention fill line assembly 14 additionally provides a means for transmitting light to and from fill line connector 26 and tourniquet instrument 12 additionally includes a cuff identification display 15, both described below and shown in detail in FIGS. 2 and 3. The current invention is equally well suited to "dual port" systems (as described by McEwen in U.S. Pat. No. 4,469,099, also typical in modern tourniquet practice), which include two separate pneumatic connections to the cuff, one for sensing the pressure within the cuff and one for supplying pressurized gas to the cuff. With a dual port system, the light transmitting means may be incorporated into either pneumatic connection or both.

Figure 2:
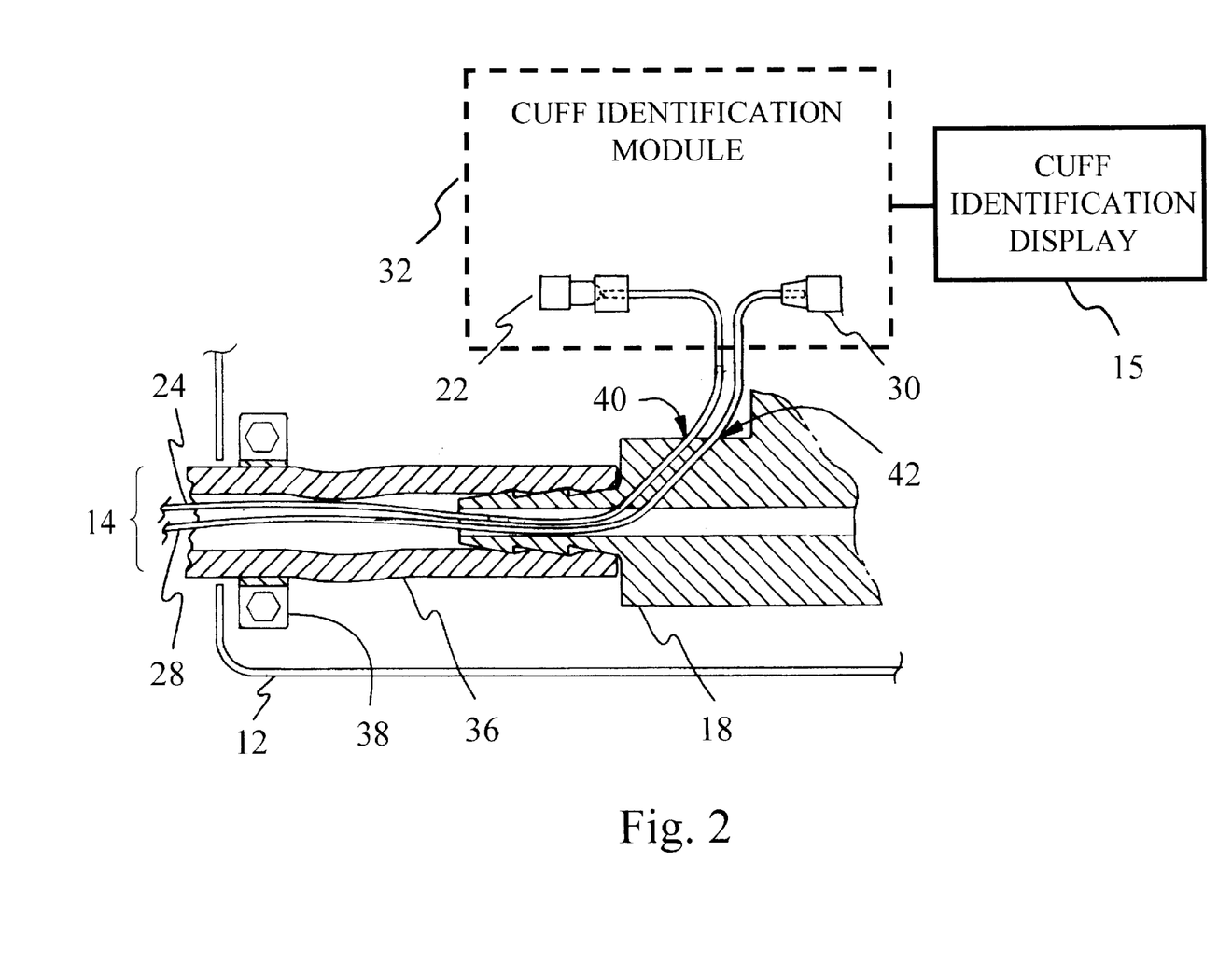
FIG. 2 is a section view through the connection arrangement between the fill line assembly and the tourniquet instrument, with a block diagram of the related instrument components.

FIG. 2 shows a section view through the connection arrangement between the fill line assembly 14 and tourniquet instrument 12, and a block diagram of the cuff identification module 32 included in instrument 12. Fill line assembly 14 comprises: hose 36 made of flexible polyurethane; fill line connector 26 shown in FIGS. 1 and 3; send fiber 24; and return fiber 28 (both made of 0.035" diameter plastic optical fiber PGR F3500, Moritex USA Inc., San Diego Calif.). Send fiber 24 and return fiber 28 lie within the lumen of hose 36 and are thus protected from damage without need for additional parts or protective sheathing on the fibers. In the preferred embodiment hose 36 has an outside diameter of 0.25 inches and an inside diameter of 0.13 inches. Hose 36 enters tourniquet instrument 12 and is secured by strain relief clamp 38. Hose 36 is coupled to a gas pressure source and regulating means 18 included in instrument 12. Send fiber 24 and return fiber 28 pass through holes 40 and 42 and are bonded in place such that a gas-tight passageway is maintained from gas pressure source 18 to the lumen of hose 36 and in turn to the inflatable bladder of the cuff attached to the system. One end of send fiber 24 is optically coupled to light emitting diode 22 and one end of return fiber 28 is optically coupled to photodiode 30. Three-color light emitting diode (LED) 22 (NSTM515AS, Nichia Corp., Tokushima, Japan) and photodiode 30 (TSL 257, Texas Advanced Optoelectronic Solutions, Plano, Tex.) are controlled by cuff identification module 32. For clarity and ease of understanding cuff identification module 32 is shown in FIG. 2 as a discrete component of instrument 12. Those skilled in the art will appreciate that cuff identification module 32 could be integrated into the control electronics and system software of instrument 12 and that communication pathways between cuff identification module and instrument 12 are present. Cuff identification module 32 communicates with cuff identification display 15 to indicate to a user the type of cuff connected to instrument 12.

Figure 3:
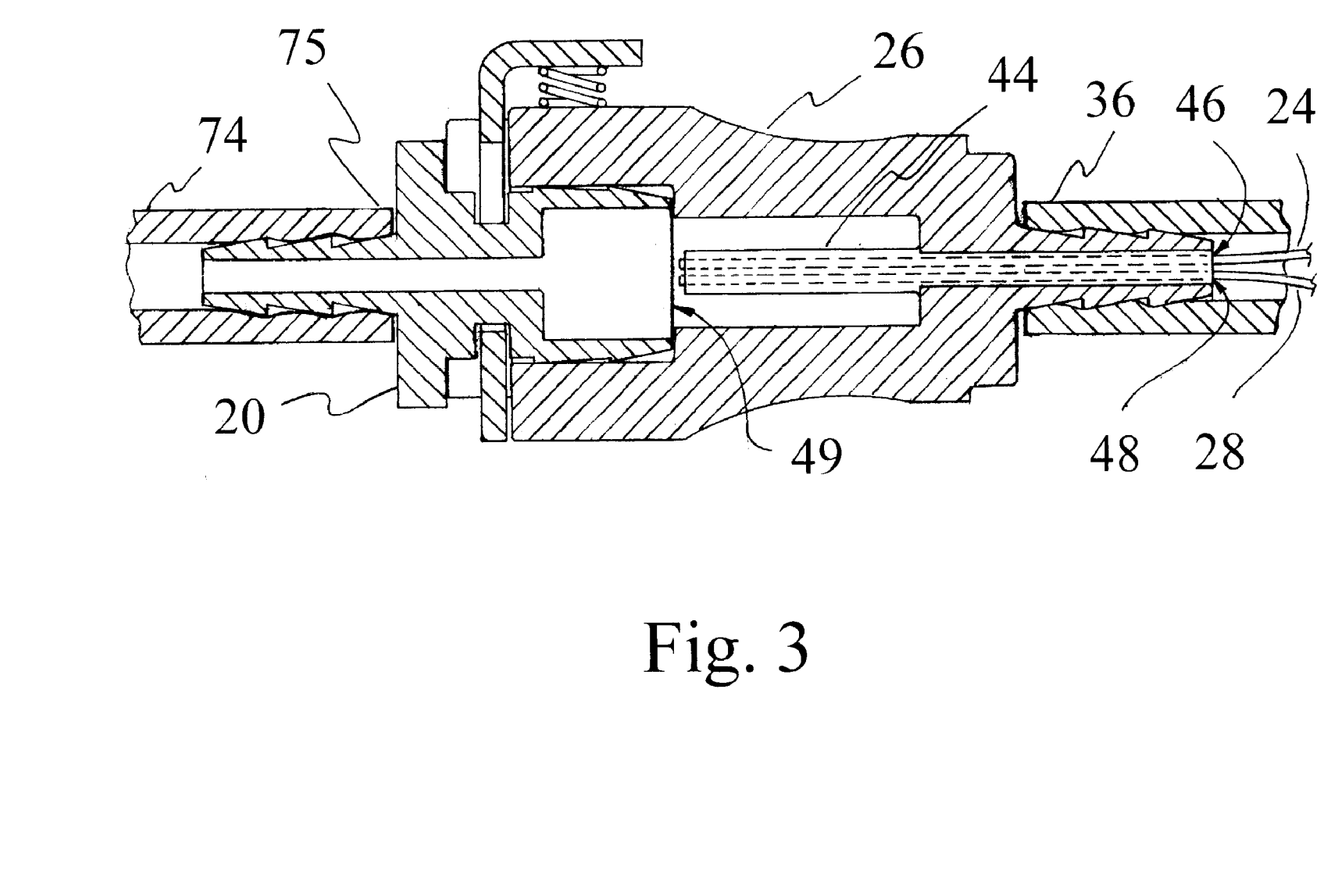
FIG. 3 is a section view through the connection arrangement between the cuff and the fill line assembly.

FIG. 3 is a sectional view through the connection arrangement between cuff 50 and fill line assembly 14 (see FIG. 1). Cuff connector 20 is permanently attached to hose 74, which in turn is permanently attached to cuff 50 (see FIGS. 4 and 5). As described above cuff connector 20 is made entirely of electrically insulating, non-conductive material of selected color and opacity, with the color corresponding to a distinct cuff type and is thus visually identifiable by the user. Cuff connector 20 and fill connector 26 are a positive locking design and produce an audible 'click' when fully engaged, maintain a gas-tight passageway when rotated relative to one another about the lumen centerline and when subjected to tension along the lumen centerline, and require a releasing force substantially perpendicular to the lumen centerline in order to be disengaged. The design of connectors 20 and 26 are based on connectors described by McEwen in U.S Pat. No. 5,649,954. For adaptation to the current invention, fill connector 26 has boss 44 incorporated in the inner bore, containing holes 46 and 48 running parallel to the inner bore. Holes 46 and 48 are of a diameter matching send fiber 24 and return fiber 28 respectively, and the fibers are bonded into holes 46 and 48 such that their ends lie within approximately 0.030 inches from the edge 49 of cuff connector 20 when the connectors 20 and 26 are fully engaged. This physical configuration of send fiber 24 and return fiber 28 within fill connector 26 permits light emitted by send fiber 24 to illuminate cuff connector 20 and light reflected from cuff connector 20 to be transmitted to instrument 12 by return fiber 28. Thus when connectors 20 and 26 are fully engaged, a pneumatic pathway is established between cuff 50 and instrument 12 and at the same time light can be transmitted between cuff connector 20 and instrument 12 allowing cuff 50 to be identified as described below. Both the pneumatic pathway and the light transmission pathway are maintained if the connectors are rotated relative to one another about the lumen centerline or subjected to tension along the lumen centerline.

The body of fill line connector 26 is preferably opaque to minimize interference and signal saturation due to high intensity ambient light (for example if the coupled connectors 20 and 26 fall under the beam of surgical lamps during use). Cuff connector 20 is manufactured to have consistent color and opacity such that the light reflected from the connector remains within predetermined limits when cuff connector 20 is rotated relative to fill line connector 26 about the lumen centerline, and such that the light reflected from mass produced colored connectors is also within predetermined tolerance limits.

It will be appreciated that other connector arrangements are possible which establish a pneumatic communication between the cuff and the instrument and a means for transmitting light between the cuff and the instrument. For example send and return fibers 24 and 28 may be arranged such that light is transmitted through cuff connector 20 (if cuff connector 20 is made from translucent material) rather reflected from cuff connector 20 as described above. Also the current invention may be adapted for dual port tourniquet systems (as described in the background) that comprise a single connector with two separate gas passageways and send and return fibers 24 and 28 applied to a selected passageway as shown in FIG. 3, or a pair of send and return fibers applied to each passageway as shown in FIG. 3.

Referring to FIGS. 1, 2, and 3, cuff identification module 32 which comprises part of instrument 12 operates as described below to determine the type of cuff connected to instrument 12 as indicated by the color of cuff connector 20. Cuff identification module 32 communicates with cuff identification display 15 and to other components within instrument 12 to indicate the type of cuff connected to instrument 12. When instrument 12 is switched on cuff identification module 32 is activated. In operation cuff identification module 32 activates LED 22 to emit a continuous series of red, green, and blue light pulses in succession (for example a 0.5 millisecond pulse of each color with a 1.5 millisecond delay between colors). The light output from LED 22 is optically coupled to send fiber 24 and transmitted to connector 26. The light pulses generated by LED 22 are emitted from send fiber 24 within connector 26 and illuminate cuff connector 20 when cuff connector 20 is engaged in fill line connector 26 to establish the gas-tight passageway between cuff 50 and instrument 12.

One end of return fiber 28 is optically coupled to photodiode 30, the other end is terminated within connector 26 such that light reflected from cuff connector 20 can be transmitted to photodiode 30. In the absence of cuff connector 20 ambient light and light reflected from the internal surfaces of connector 26 is transmitted to photodiode 30.

Cuff identification module 32 monitors the intensity level of light detected by photodiode 30. By recording the detected intensity levels at the times when red, green and blue light is being emitted from LED 22 and when LED 22 is inactive, cuff identification module 32 can compute the relative intensities of red, green and blue light reflected from cuff connector 20 and the intensity of ambient light detected when LED 22 is inactive. The detected intensity levels of ambient light recorded when LED 22 is inactive are used by cuff identification module 32 to compensate for variations in ambient lighting conditions and detect error conditions such as the complete saturation of photodiode 30. The computed relative intensity levels of red, green and blue light reflected by cuff connector 20 are compared by cuff identification module 32 to predetermined ranges of relative intensities stored within cuff identification module 32 and corresponding to each cuff in cuff set 16. The cuff type is determined when a predetermined number of reflected light pulses (for example five consecutive series of red, green and blue light pulses) all have relative intensities falling within the predetermined range matching the cuff type. Once identified, the cuff type and/or related predetermined information may be displayed on cuff identification display 15 and recorded within cuff identification module 32, information from other components within instrument 12 such as time and date, pressure setting, and tourniquet inflated time may also be recorded by cuff identification module 32.

The colors corresponding to the various different cuff types in cuff set 16 are selected to produce distinct relative intensity levels of reflected red, green and blue light. Cuff identification module 32 may be initially calibrated in order to adjust the stored predetermined ranges of relative intensities corresponding to specific cuff types to compensate for changes in component specifications and manufacturing variations. Calibration may be performed by using a series of reference colored connectors, and similarly re-calibration may be performed in the field by the user or by service personnel.

An example of the operation of cuff identification module is as follows. When a specific type of cuff from cuff set 16 having a red colored connector is connected to fill line assembly 14, green and blue light pulses generated by LED 22 are absorbed by the red colored connector to a greater degree than the red light pulses generated by LED 22. Consequently the intensity of the red light pulses reflected from the red colored connector relative to the intensity of the reflected green and blue light pulses is greater. Cuff identification module 32 will identify the attached cuff as corresponding to a specific type having a red connector by comparing the relative intensities of the light reflected from the red colored cuff connector and sensed by photodiode 30 to a predetermined selection of stored relative intensity values.

Cuff identification module 32 in conjunction with instrument 12 also operates to detect potentially hazardous conditions. During operation cuff identification module 32 continuously monitors the absolute intensity levels of the reflected red, green and blue light pulses and the intensity level of ambient light when LED 22 is inactive. A sudden drop in intensity levels indicates possible disengagement of connectors 20 and 26 or a kink in hose 36. If hose 36 and fibers 24 and/or 28 are kinked such that the specified minimum bend radius of the fiber(s) is exceeded, the intensity level of light detected by photodiode will be reduced as light can no longer be transmitted by the optical fibers. If a sudden reduction in detected light levels is concurrent with falling cuff pressure and a corresponding high demand for pneumatic pressure from instrument 12, warning of a possible disconnection at connectors 20 and 26 may be activated. If signal loss is not accompanied by loss of pressure or high demand for pneumatic pressure from instrument 12, warning of a possible kink in hose 36 may be activated.

Cuff identification module 32 can, by recording the intensity levels of detected light over a number of uses, enable various automatic system optimization and self-calibration functions. For example a gradual reduction in detected light levels over time or a number of uses may indicate wear and degradation of the fill line assembly 14 and a service advisory message may be displayed. Similarly, changes in light levels corresponding to a particular type of cuff over time may activate a self-calibration function or service advisory.

Figure 4:
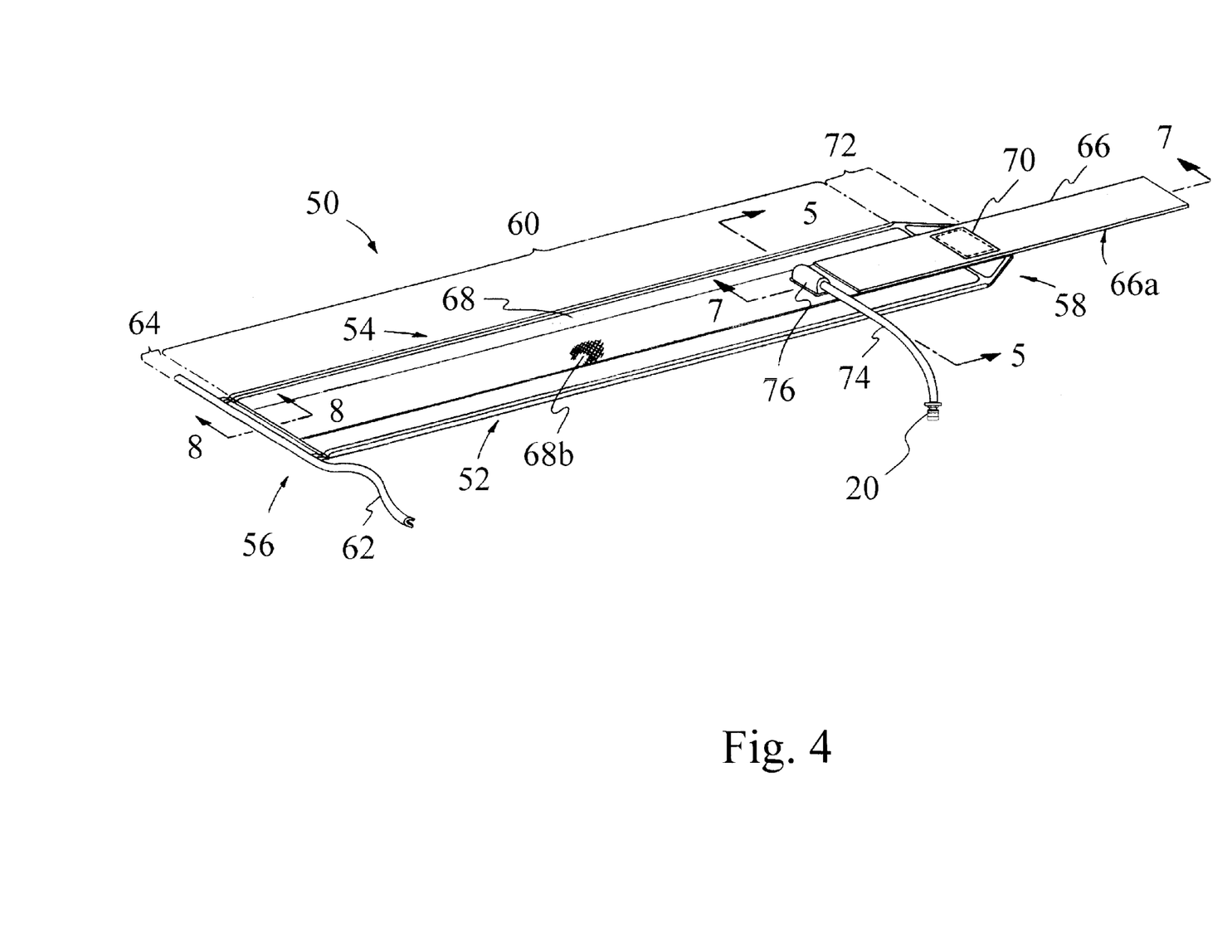
FIG. 4 is a view of a typical low-cost cuff included in the tourniquet system.

FIG. 4 is a view of a typical cuff 50 included in the tourniquet system. The embodiment shown applies in general to the different sizes and shapes of cuffs that may be included in a set of cuffs included in the tourniquet system. Cuff 50 has proximal side 52, distal side 54, fixed end 56, overlapping end 58, and bladder 60 having a length selected to be sufficient for the bladder 60 to encircle the limb at a desired location and overlap on itself in a substantially circumferential direction. For illustrative purposes cuff 50 is shown with dimensions suitable for encircling a cylindrical limb of up to 23 inches in circumference. Accordingly a suitable length of bladder 60 is 24 inches, a suitable overall width of cuff 50 is 4 inches, and the bladder 60 is rectangular when the cuff is laid flat.

Tie ribbon 62 is made of ⅝" wide nylon ribbon (Grosgrain ⅝" wide, Dynatex Textiles Inc., Toronto, Ontario, Canada) and is permanently attached to the cuff in the non-inflating portion 64 near fixed end 56. A suitable length of non-inflating portion 64 is 0.50 inches. Strap 66 is made of 2" wide woven hook material with hook-type fastening surface 66a facing the limb. A portion (a suitable length being 6 inches) of strap 66 engages loop-type fastening surface 68b of outer strip 68 between port manifold 76 and overlapping end 58, and the remaining length (a suitable length being 8 inches) forms the free portion of strap 66 extending beyond overlapping end 58. It will appreciated that the locations of the hook and loop fastening surfaces may be reversed, in which case a thermoplastic hook material (such as 2" wide HTH848, Velcro USA Inc., Manchester N.H.) is incorporated into outer strip 68 and strap 66 is made from 2" wide woven loop material. It will also be appreciated that alternate fastening means are possible; for example a pressure-sensitive adhesive could be used in place of hook-type fastening surface 66a, in which case loop-type fastening surface 68b may be eliminated and outer strip 68 strap must be a smooth surface suitable for engaging the adhesive. This arrangement may allow lower cost manufacture but is only appropriate for a single use disposable cuff in which the fastening means is only engaged once, and may make the cuff difficult for the user to reapply or reposition during use.

Label 70 is made of nylon material printed with selected information for the user and is permanently sewn to the cuff through strap 66 and non-inflating portion 72. A suitable length of non-inflating portion 72 is 1.5 inches. It will be apparent to one skilled in the art that other joining methods (such as bonding) may be selected to permanently attach strap 66 and label 70 to the cuff.

In typical use fixed end 56 is held against the limb while the cuff is wrapped around the limb and pulled snug by applying tension at overlapping end 58 approximately tangent to the curve of the limb while fixed end 56 is held stationary relative to the limb by grasping tie ribbon 62. Strap 66 secures the cuff circumferentially around the limb when the user engages its free portion to the loop-type fastening surface 68b on the outer surface of the cuff. Thus engaged, strap 66 and outer strip 68 form a complete circumferential tensile load path defining a substantially fixed outer circumference of the cuff. The cuff therefore expands radially inward towards the limb when bladder 60 is inflated and applies radial compression to the limb proportional to the pressure in bladder 60, which is selected to safely occlude blood flow in the limb across the region of the cuff.

Hose 74 is made of vinyl tubing and is permanently bonded at one end to port manifold 76, forming a gas-tight passageway into bladder 60. Cuff connector 20 (described in FIGS. 1–3) is permanently attached to hose 74 at the remaining end. Depending on the tourniquet instrument used, cuff 50 may alternately have a plurality of gas-tight passageways into bladder 60 and a corresponding number of gas-tight passageways through port manifold 76, hoses, and connectors.

Referring to FIGS. 1, 3, and 4, hose 74 is typically included in sterile, disposable cuffs to provide an extension of the gas passageway a convenient distance from the sterile cuff. This allows connection to the non-sterile fill line assembly 14 attached to the tourniquet instrument at a point safely outside the sterile surgical field. It will be appreciated that hose 74 may be made of a selected distinctly colored thermoplastic material suitable for cuff identification as described above and formed at end 75 to connect pneumatically to fill line connector 26, thereby providing pneumatic connection and identification means and eliminating the need for a separate cuff connector 20. It will also be appreciated that identification means perceptible to the user and identifiable by tourniquet instrument 12 may be incorporated by using a distinctly colored port manifold 76 permanently attached to cuff 50 in which case connectors 20 and 26 and hose 74 are adapted to transmit light signals as well as pressurized gas to the cuff. For cuff designs in which hose 74 is not required cuff connector 20 may be attached directly to port manifold 76 or incorporated into port manifold 76 as a single component.

Figure 5:
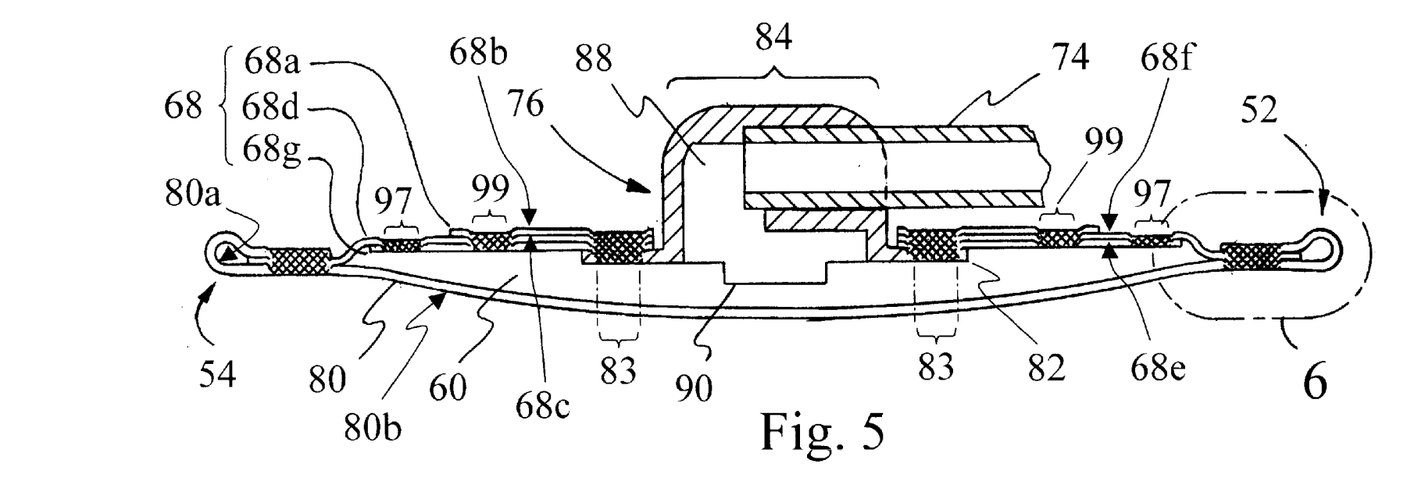
FIG. 5 is cross sectional view through the cuff and the port manifold.

FIG. 5 is cross sectional view through the cuff in the region of bladder 60 and passing through port manifold 76. Outer strip 68 and inner strip 80 are gas impermeable and are bonded together to form an inflatable bladder (the bonding arrangement is described in detail below). Outer strip 68 and inner strip 80 are continuous strips (long, narrow pieces each having substantially uniform width) which are particularly suited for a continuous manufacturing process which is described in more detail below. Outer strip 68 is comprised of loop material 68a (LP3607 "RF weldable" loop, 2 inches wide, Velcro USA Inc., Manchester N.H.), flexible gas impermeable layer 68d (DuPont 'Sontara' 8005 polyester non-woven fabric, DuPont Nonwovens Wilmington Del., with 0.009" thick AlphaGary 2222RX-78 flexible polyvinylchloride (PVC) coating supplied by Wiman Corp., Sauk Rapids, Minn.), and stiffening layer 68g (0.020 thick rigid PVC sheet #1204, PMC Films, Tottenham, Ontario, Canada). Flexible gas impermeable layer 68d has plain thermoplastic surface 68e on the side facing the limb and soft, fuzzy fabric surface 68f on the opposite face. Preferably surface 68f does not act like a loop-type fastening surface and therefore will not accidentally engage hook-type fastening surfaces included in the cuff or other devices used near the cuff. Loop material 68a has loop-type fastening surface 68b which faces away from the limb and thermoplastic surface 68c on the opposite side, lying against fabric surface 68f of flexible gas impermeable layer 68d. Due mainly to the thickness and material stiffness properties selected for stiffening layer 68g, outer strip 68 is substantially inextensible in the circumferential direction and is substantially more resistant to outward bending (greater outward radial expansion along a midline equidistant to proximal and distal sides 52 and 54 than at sides 52 and 54) than inner strip 80, thereby maintaining a substantially fixed outer circumference when the cuff is pressurized up to 500 mmHg and restricting expansion of the cuff to a radially inward direction, which in turn applies radial pressure to the limb. Furthermore the selection of a width of stiffening layer 68g that is narrower than the width of bladder 60 makes outer strip 68 stiffer near the midline of the cuff and relatively more flexible near proximal and distal sides 52 and 54. This varying stiffness across the cuff width is essential to allow the cuff to expand inwards (and thereby occlude blood flow at safe pressures) without excessive inward kinking and distortion of stiffening layer 68g along its edges near sides 52 and 54. In the preferred embodiment, stiffening layer 68g is made of thicker, stiffer material than flexible gas-impermeable layer 68d. It will be appreciated that a similar variation in stiffness between the midline of the cuff and the sides may be achieved by means other than varying thickness, such as selection of a wider and stiffer loop material 68a or increasing the material stiffness properties of flexible gas-impermeable layer 68d in the middle region only.

The components of outer strip 68 are bonded together along the proximal and distal sides of the cuff at stiffener edge bond 97 and loop edge bond 99. A suitable width for both bonds 97 and 99 is 0.13 inches. In the preferred embodiment stiffener edge bond 97 is continuous and gas-impermeable in order to prevent inflation of the space between flexible gas impermeable layer 68d and stiffening layer 68g, although this is not essential to operation of the cuff and any joining arrangement that retains the gas-impermeability of flexible layer 68d and has sufficient strength may be used (for example an intermittent ultrasonic weld). Loop edge bond 99 is preferably continuous but may be substituted with an intermittent bond of sufficient strength that does not affect the gas-impermeability of flexible layer 68d. Loop edge bond 99 also preferably engages stiffening layer 68g as shown (to pass shear loads from loop-type fastening surface 68*b* to stiffening layer 68*g*) but again this is not essential to the operation of the cuff if shear and tensile loads can be suitably carried by selected materials 68*a* and 68*d*.

It will be appreciated that flexible layer 68*d* and stiffening layer 68*g* could be integrated by using a single piece of thermoplastic material extruded to form a section thicker (and thereby stiffer) in the middle region of the cuff and thinner at the proximal and distal sides 52 and 54, in which case bond 97 would be eliminated.

It will be also be appreciated that outer strip 68 could be made of a single piece of thermoplastic material with a suitable hook or loop type fastening surface (for example a material similar to Velcro HTH848) with a cross section selected to be thicker in the middle region of the cuff and thinner near the proximal and distal sides 52 and 54, in which case bonds 97 and 99 would be eliminated.

As the outline of the bonded areas is visible (particularly in the loop surface 68*a* where the loop is flattened by the bonding process), the shape of bonds 97 and 99 in the plane of outer strip 68 may form markings such as symbols or letters in selected areas. These markings may be used to further identify the cuff to the user and to display other information such as the cuff range limits. Also, such markings may be adapted to align with other markings and/or specified features of the cuff when the cuff is applied and thereby indicate whether or not the cuff is applied to a limb within the circumference range limits of the cuff.

Inner strip 80 has a thermoplastic surface 80*a* compatible for bonding to outer strip 68 and soft, fuzzy surface 80*b* facing the limb. Preferably surface 80*b* does not act like a loop-type fastening surface and therefore will not accidentally engage hook-type fastening surfaces included in the cuff or other devices used near the cuff. Inner strip 80 is preferably made of nonwoven polyester fabric (DuPont Sontara 8005) coated on surface 80*a* with 0.009 thick flexible PVC. In the preferred embodiment inner strip 80 and flexible gas impermeable layer 68*d* are made of the same material. Although the strength and aesthetic appeal of the cuff may be reduced, it will be appreciated that for additional cost savings and for easier bonding the fabric backing may be eliminated from all or part of flexible gas impermeable layer 68*d* (resulting in a plain thermoplastic surface on all or part of side 68*f*). Alternatively, other materials may be used in layers 68 and 80; For example thermoplastic polyurethanes and woven fabrics may be used rather than PVC and non-woven fabrics for applications requiring greater strength and durability such as larger size cuffs and non-disposable cuffs intended for repeated uses.

Also shown is gas passageway 88 in port manifold body 84. Hose 74 is permanently bonded to port manifold body 84 by solvent bonding. Gas passageway 88 exits body 84 in a direction parallel to the plane of outer strip 68 and also roughly perpendicular to proximal side 52. Thus when the cuff is applied to the limb properly, gas passageway 88 and hose 74 point proximally (away from the surgical site), minimizing the chance of the hose encroaching on the surgical field. If desired, port manifold 76 can be oriented in any direction within the plane of outer strip 68 as required to suit the intended use of the cuff. For example if it is desired that the cuff may be applied with either side 52 or 54 towards the proximal end of the limb, port manifold 76 may be oriented such that gas passageway 88 exits roughly parallel to side 52 or 54. Port manifold bond 83, which is continuous around the perimeter of port manifold flange 82, and anti-occlusion boss 90 are also shown and are described in detail in the description of FIG. 7. A suitable width for anti-occlusion boss 90 as seen in FIG. 5 is 0.31 inches.

Figure 6:
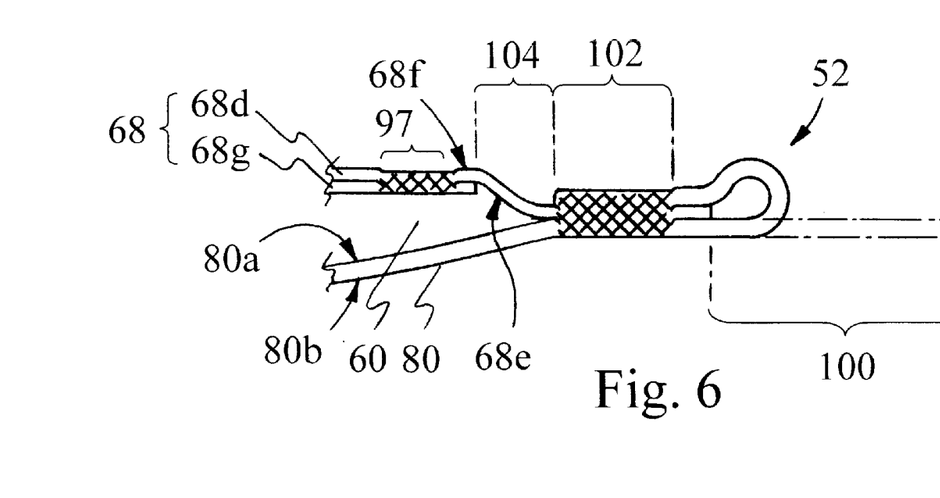
FIG. 6 is a detail section of the folding and bonding arrangement along the side edges of the cuff.

FIG. 6 is a detail section of the bonding arrangement along side 52 of the cuff. An identical bonding arrangement is used along side 54 seen in FIG. 5. Inner strip 80 is wider than outer strip 68, with folded portion 100 extending beyond the side edge of the outer strip by a selected distance (a suitable distance being 0.38 inches). The folded portion 100 is folded up and over the side edge of outer strip 68 before bonding. Bladder side seal 102 extends uninterrupted at least the full length of bladder 60 and comprises a gas-impermeable bond between the thermoplastic surface 80*a* of inner strip 80 and thermoplastic surface 68*e* of flexible gas-impermeable layer 68*d*. During the formation of seal 102 the folded portion 100 of inner strip 80 is bonded to soft, fuzzy surface 68*f* of flexible layer 68*d*, retaining the folded-over material and thereby forming a rounded edge along the sides of the cuff with soft, fuzzy surface 80*b* exposed to the limb. This folded edge arrangement eliminates the need for the costly sewn edge trim used along the edges of many cuffs in the prior art to protect the patient from chafing. A suitable width of bladder side seal 102 is 0.19 inches. To allow the cuff to expand inwards when inflated without distorting the edges of stiffening layer 68*g*, gap 104 is provided between the outer edge of the stiffening layer 68*g* and the inner edge of the bladder side seal 102. A suitable gap 104 is 0.13 inches. Also visible in this detail section is stiffener edge bond 97.

Although potentially more difficult to fold and bond, flexible gas impermeable layer 68*d* could be made the same width as inner strip 80 and folded over along with inner strip 80, thereby forming a stiffer edge along sides 52 and 54. In this case soft, fuzzy surface 68*f* of flexible gas impermeable layer 68*d* is folded back on itself and bonded together during the formation of seal 102, thus retaining the folded-over material and forming a rounded edge along the sides of the cuff.

It will be appreciated that other less desirable folding arrangements are possible which achieve a rounded edge along the sides of the cuff. For example outer strip 68 could lie on top of the folded portion of inner strip 80 in the region of seal 102, such that thermoplastic surface 68*e* lies against soft, fuzzy surface 80*b* although this arrangement may be less reliable because the primary bond forming the bladder must penetrate through fuzzy material. As another example, the edges of flexible layer 68*d* and inner strip 80 could butt together when inner strip 80 is folded over, in which case the width of seal 102 would have to extend a suitable distance either side of the butt joint and therefore may increase overall cuff width and be more difficult to manufacture.

As described in the background to the invention, many existing tourniquet cuffs include an edge trim (a separate band of material such as nylon ribbon) folded over the outer perimeter edge of the cuff and sewn through all layers outside the bladder perimeter. The 'Comforter™ Disposable Gel Cuff' uses a portion of the inner layer material folded over the perimeter edge and sewn outside the bladder perimeter in place of a separate edge trim. In both these examples of prior art the edge arrangement protects the patient from injury due to chafing or contact with the raw material edges at the perimeter of the cuff. However sewing the edge trim or folded-over inner layer outside the bladder perimeter produces a narrower bladder for a given overall cuff width. In contrast the current invention maximizes the bladder width within a given overall cuff width by incorporating the folded-over portion of the inner material layer (which serves the function of the edge trim used in the prior art) into the bladder bonds. As a result the present invention allows occlusion at lower cuff pressures on a given limb for a given overall cuff width compared to the prior art, thereby maximizing access to the limb for surgery and minimizing the risk of pressure related injury to the patient.

Although stability of the cuff may be reduced, the width of bladder 60 could be further maximized for a given overall cuff width by allowing bladder side seal 102 to form a gas-impermeable bond between thermoplastic surface 80*a* in the folded portion 100 and fuzzy surface 68*f* only, such that thermoplastic surface 68*e* does not bond to inner layer thermoplastic surface 80*a*. This may be achieved by coating one or both surfaces 68*e* and 80*a* with a bond inhibiting material (for example 'Mold Wiz AZN' release agent, Axel Plastics Research Laboratories Inc., NY) in the region of seal 102.

Figure 7:
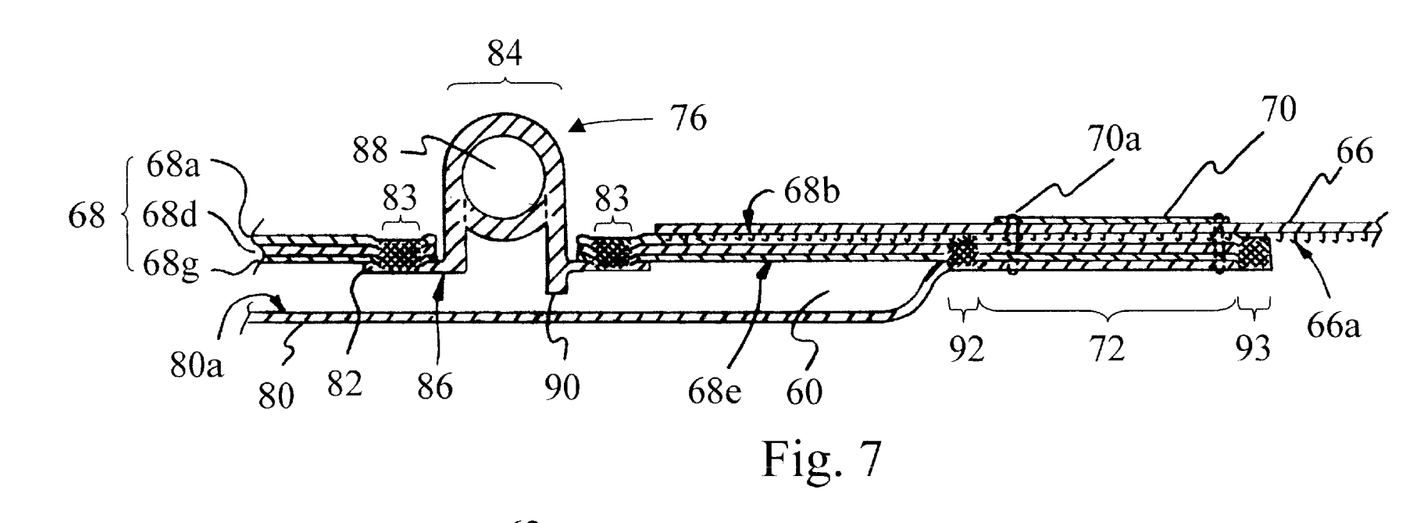
FIG. 7 is a longitudinal section through the cuff at the overlapping (strap) end.

FIG. 7 is a longitudinal section through the cuff at the overlapping end 58 near strap 66. Port manifold 76 is bonded to outer strip 68 around the perimeter of port manifold flange 82 at a selected location within bladder 60. The outer perimeter of flange 82 extends outward from the perimeter of body 84 in all directions in the plane of outer strip 68 by a distance sufficient for bonding, for example 0.25 inches. This arrangement allows bonding means (such as an ultrasonic die) to approach the cuff assembly in a single direction approximately perpendicular to the plane of outer strip 68. Port manifold bond 83 forms a continuous, gas impermeable bond between outer strip 68 and port manifold 76 around the perimeter of port manifold flange 82. A suitable width for bond 83 is 0.19 inches. To allow bonding of port manifold 76 to outer strip 68 with inner strip 80 in place without bonding flange 82 to inner strip 80 as well, which may be desirable in certain versions of the manufacturing process, flange inner surface 86 may be covered with bond inhibiting material (for example 'Mold Wiz AZN' release agent, Axel Plastics Research Laboratories Inc., NY).

Port manifold 76 has gas passageway 88 passing through body 84 into bladder 60, and also includes at least one anti-occlusion boss 90 which protrudes into bladder 60 (by a suitable distance such as 0.063 inches from the plane of flange inner surface 86) and has a thickness of about 0.063 inches. Alternately for the dual port systems described in the background, port manifold 76 can have two separate gas passageways passing through body 84 into bladder 60. Anti-occlusion boss 90 prevents inner strip 80 from blocking gas passageway 88, for example if inner strip 80 is pressed against flange inner surface 86 with an unusually high force during application or use. If required, additional gas passageways of various sizes could be incorporated into port manifold 76, and a plurality of anti-occlusion bosses may be used to suit the size and shape of gas passageway 88 and flange 82 as well as the number of gas passageways in port manifold 76.

Bladder end seal 92 at overlapping end 54 forms an end of bladder 60 and is described in more detail below. Around the remaining perimeter of non-inflating portion 72, overlapping end edge bond 93 joins the edges of inner strip 80 and outer strip 68. Also shown are label 70 and sewn joint 70*a* around the perimeter of the label, passing through strap 66 and all layers of the cuff in non-inflating portion 72. Strap 66 is redundantly attached to the cuff via engagement of hook-type fastening surface 66*a* and loop-type fastening surface 68*b*.

Depending on the sequence of manufacturing operations, sewn joint 70*a* may engage outer strip 68 only. Also depending on the sequence of manufacturing operations and the materials used, other joining methods (such as bonding) may be used in place of sewn joint 70*a*.

Figure 8:
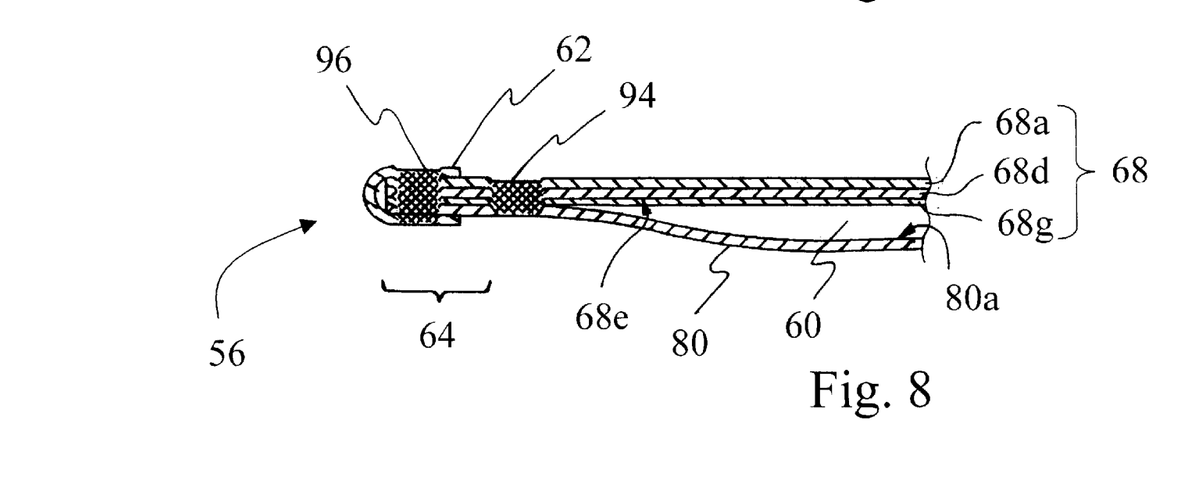
FIG. 8 is a longitudinal section through the cuff at the fixed (tie ribbon) end.

FIG. 8 is a detail longitudinal section through the cuff at fixed end 56 near tie ribbon 62, which is folded over the ends of outer strip 68 and inner strip 80, thus protecting the patient's skin from the raw edge and square corners of the stiffener portion 68*g* of outer strip 68. Bladder end seal 94 at fixed end 56 forms an end of bladder 60 and is described in more detail below.

Tie ribbon 62 is made of synthetic material and therefore may be bonded to outer and inner layer materials 68 and 80 at fixed end bond 96. Non-inflating portion 64 allows for attachment of tie ribbon 62 without interfering with and compromising the integrity of the critical bladder end seal 94. A suitable width for fixed end bond 96 is 0.25 inches. It will be appreciated by those skilled in the art that with certain combinations of materials and bonding processes, tie ribbon 62 may be suitably retained by bladder end seal 94, allowing non-inflating portion 64 and fixed end bond 96 to be eliminated for a potential reduction of material and manufacturing cost. It will be further appreciated that, although potentially more costly to manufacture, tie ribbon 62 may be sewn conventionally through non-inflating portion 64, eliminating the need for fixed end bond 96 and allowing use of tie ribbon materials not suited for bonding.

Referring to FIGS. 4, 6, 7 and 8, bladder end seals 92 and 94 each extend at least across the width of bladder 60 and intersect the bladder side seal 102 at both the proximal and distal sides 52 and 54 of the cuff. Across the entire width of stiffening layer 68*g*, bladder end seals 92 and 94 form gas-impermeable bonds between the thermoplastic surface 80*a* of inner strip 80, stiffening layer 68*g*, and thermoplastic surface 68*e* of flexible layer 68*d*. Loop material 68*a* is also bonded to outer strip 68 in the area of seals 92 and 94. Over the span of each gap 104 from the edge of stiffening layer 68*g* to bladder side seal 102, seals 92 and 94 form gas-impermeable bonds between the thermoplastic surface 80*a* of inner strip 80 and thermoplastic surface 68*e*. It will be appreciated that seals 92 and 94 may extend across the overall width of the cuff, joining any excess width of flexible layer 68*d* extending outside seal 102 to surface 80*a* and further joining any remaining portion of surface 80*a* to itself in folded portion 100. A suitable width of seals 92 and 94 as seen in FIGS. 7 and 8 is 0.19 inches.

To achieve low manufacturing cost and a simple continuous manufacturing process as described below, inner strip 80 has a constant cross section along its length, and outer strip 68 has a constant cross section along its length except in the area adapted for attaching port manifold 76. Therefore the varying stiffness property across the width of outer strip 68 necessarily continues through bladder end seals 92 and 94. In the preferred embodiment seals 92 and 94 each have a uniform thickness of 0.040 inches across the overall width of the cuff after the seal is fully formed. It will be appreciated that due to the different thickness, stiffness, and composition of the materials joined by seals 92 and 94 at various points across the overall width of the cuff, the seal may be improved by using a stepped sealing die producing a non-uniform seal thickness, for example allowing for increases in seal thickness across the widths of stiffening layer 68*g* and loop material 68*a*. However this potential improvement adds manufacturing complexity because the various components must be more carefully aligned relative to the sealing die. Manufacture of cuff 50 may proceed as follows:

a) Loop 68*a*, flexible gas impermeable layer 68*d* and stiffening layer 68*g* are supplied at net width on rolls, a suitable length being 100 yards and suitable widths of 2 inches, 3 inches, and 3.75 inches respectively. Outer strip 68 is constructed by aligning materials 68a, 68d and 68f as shown in FIG. 5 and feeding the aligned materials through a continuous ultrasonic bonding process comprised of four drive wheel/anvil sets forming bonds 97 and 99. A suitable feed rate using conventional ultrasonic sewing equipment and the materials described in the preferred embodiment is 10 feet per minute.

b) Openings allowing the body portion 84 of port manifold 76 to pass through outer strip 68 are then die cut in outer strip 68 at intervals corresponding to the particular cuff length being manufactured. A port manifold 76 is inserted in each opening and bond 83 around the perimeter of flange 82 is formed using a press-type ultrasonic or radio frequency sealing apparatus. A dwell in the continuous process, with infeed and outfeed rates suitable to match the port manifold sealing rate to the continuous rate of the outer layer bonding process, may be required for installing the port manifold.

c) Inner strip 80, supplied on rolls at net width (for example 100 yards long and 4.50 inches wide), is then aligned with outer strip 68 and fed through folding infeed apparatus to form the folded edge arrangement shown in FIGS. 5 and 6. A folding foot, commonly used to feed the folded edge trim used on many prior art cuffs and other sewn products into conventional sewing machines, may be adapted for this purpose. A pair of ultrasonic drive wheel/anvil sets form continuous gas-impermeable bonds 102 as shown in FIGS. 5 and 6 in a manner similar to bonds 97 and 99 of the outer strip, thus forming a continuous strip of assembled layers with port manifolds in place.

d) A single press-type ultrasonic or radio frequency sealing die is used to form seal 92 and bond 93 (shown in FIG. 7) at the overlapping end 58 of one cuff on the continuous strip of assembled layers, and seal 94 (shown in FIG. 8) at fixed end 56 of the adjacent cuff on the continuous strip. Similarly a single cutting die separates the cuffs by cutting through bond 93 and cutting across the cuff width at fixed end 56 an appropriate distance from seal 94 to form non-inflating portion 64. Cuff length is not restricted by the size of the equipment and any length of cuff may be produced by adjusting the spacing between the port manifolds and the end seals.

e) Tie ribbon 62 is introduced across fixed end 56 (as shown in FIG. 8) using a folding infeed (similar to that used for the folded side edges) and bond 96 is formed using a press-type ultrasonic or radio frequency sealing die. A dwell in the continuous process, with infeed and outfeed rates suitable to match the continuous rate of the outer layer bonding process, may be required for installing the tie ribbon.

f) Strap 66, supplied at a stock width (such as 2 inches) and cut to a length appropriate for the cuff size being manufactured, is then applied to each cuff with hook surface 66a engaging loop surface 68b with one end abutting port manifold 76. Label 70 is positioned over non-inflating portion 72 and sewn or bonded in place through the entire assembly as shown in FIG. 7. This completes fabrication of the cuff.

If greater manufacturing flexibility desired, for example to produce smaller quantities of a particular cuff size with minimal equipment setup time, the stages of the manufacturing process for the current invention as described above may be separated. For example since a common cuff width is often used for various cuff lengths, operations (a) and (c) above may be run to produce lengths of assembled inner and outer layer material. Such bulk material may later be cut off to the lengths required and the cuffs completed by installing the port manifolds, forming the end seals, and installing the tie ribbon and strap. In this case the die cutting and sealing equipment required is much smaller and less expensive than the equipment used in the prior art, equipment setups are common among all cuff sizes of the same width, and cuffs of any length may be produced.

It is to be understood that the invention is not to be limited to the details herein given but may be modified within the scope of the appended claims.

We claim:

1. A low cost tourniquet cuff with identification apparatus, comprising:

an outer strip;

an inner strip positioned against the outer strip;

a gas-tight seal joining the inner strip to the outer strip to form a cuff having a physical characteristic wherein the cuff includes an inflatable bladder of a length greater than the circumference of a limb at a selected location; and a cuff connector carried on the cuff and communicating pneumatically with the bladder for releasably connecting to a tourniquet instrument to establish a gas-tight passageway between the bladder and the instrument, wherein the cuff connector includes identification means indicative of the physical characteristic and detectable by the tourniquet instrument upon establishment of the gas-tight passageway irrespective of whether the gas-tight passageway is pressurized.

2. The tourniquet cuff of claim 1 wherein the connector is entirely formed of electrically insulating material.

3. The tourniquet cuff of claim 1 wherein the identification means is further visibly perceptible by a user of the cuff.

4. The tourniquet cuff of claim 1 wherein:

the outer strip has first and second side edges, a first thickness along the outer strip at a first predetermined distance from the first side edge and a second thickness along the outer strip at a second predetermined distance from the first side edge, wherein the second predetermined distance is greater than the first predetermined distance;

the inflatable bladder formed by the gas-tight seal has two bladder ends, two bladder sides and a bladder midline between the two bladder sides; and wherein at the bladder ends the outer strip has the second thickness at the bladder midline and the first thickness at a location between the bladder midline and a bladder side.

5. The tourniquet cuff of claim 1 wherein:

the inner strip has side edges and a side edge surface along each side edge;

the gas-tight seal has an inner perimeter and an outer perimeter, and wherein the inner strip is folded so that the side edge surfaces face toward the bladder midline and are located within the outer perimeter.

6. A low cost tourniquet cuff with identification apparatus, comprising:

an outer strip;

an inner strip positioned against the outer strip;

a gas-tight seal joining the inner strip to the outer strip to form a cuff having a physical characteristic wherein the cuff includes an inflatable bladder of a length greater than the circumference of a limb at a selected location;

a cuff connector carried on the cuff and communicating pneumatically with the bladder for releasably connecting to a tourniquet instrument to establish a gas-tight passageway between the bladder and the instrument, wherein the cuff connector includes identification means indicative of the physical characteristic and detectable by the tourniquet instrument upon establishment of the gas-tight passageway; and a tourniquet instrument responsive to the identification means for producing a signal indicative of the detected physical characteristic after establishment of the gas-tight passageway and wherein the instrument further includes means for supplying gas to the bladder through the passageway at a pressure sufficient to stop arterial blood flow into the limb distal to the cuff.

7. The tourniquet cuff of claim 6 wherein the identification means is a selected color from a predetermined number of predetermined colors, each color corresponding to a predetermined physical characteristic, and wherein the instrument produces the signal by detecting the selected color.

8. A low cost tourniquet cuff with identification apparatus, comprising:

an outer strip;

an inner strip positioned against the outer strip;

a gas-tight seal joining the inner strip to the outer strip to form a cuff having a physical characteristic wherein the cuff includes an inflatable bladder of a length greater than the circumference of a limb at a selected location;

a cuff connector carried on the cuff and communicating pneumatically with the bladder for releasably connecting to a tourniquet instrument to establish a gas-tight passageway between the bladder and the instrument, wherein the cuff connector includes identification means indicative of the physical characteristic and detectable by the tourniquet instrument upon establishment of the gas-tight passageway; and wherein the physical characteristic identifies the manufacturer of the cuff.

9. A low cost tourniquet system with identification apparatus, comprising:

a tourniquet cuff having an inflatable bladder of a length sufficient for encircling a limb at a selected location;

a connector carried on the cuff and communicating pneumatically with the bladder for releasably connecting the cuff to a tourniquet instrument to establish a gas-tight passageway between the bladder and the instrument, wherein the connector includes identification means indicative of a physical characteristic of the cuff; and a tourniquet instrument for supplying pressurized gas to the bladder through the gas-tight passageway established by the connector, wherein the instrument includes detection means responsive to the identification means after establishment of the gas-tight passageway and, irrespective of whether pressurized gas is supplied through the gas-tight passageway, for producing a signal indicative of the physical characteristic.

10. A low cost tourniquet cuff, comprising:

an outer strip having first and second side edges, a first thickness along the outer strip at a first predetermined distance from the first side edge and a second thickness along the outer strip at a second predetermined distance from the first side edge, wherein the second predetermined distance is greater than the first predetermined distance such that the outer strip is thickened away for the first and second side edges;

an inner strip positioned against the outer strip;

a gas-tight seal joining the outer strip to the inner strip to form an inflatable bladder having two bladder ends, a bladder length between the two ends greater than the circumference of a limb at a selected location, two bladder sides and a bladder midline between the two bladder sides; and wherein at the bladder ends the outer strip has the second thickness at the bladder midline and the first thickness at a location between the bladder midline and a bladder side.

11. The tourniquet cuff of claim 10 and including a cuff connector communicating pneumatically with the bladder for releasably connecting to a tourniquet instrument to establish a gas-tight passageway between the bladder and the instrument, wherein the cuff connector includes identification means indicative of a physical characteristic of the cuff and detectable by the tourniquet instrument upon establishment of the gas-tight passageway and in a manner that is independent of pressure within the gas-tight passageway.

12. A low cost tourniquet cuff, comprising:

an outer strip having first and second side edges, a first thickness along the outer strip at a first predetermined distance from the first side edge and a second thickness along the outer strip at a second predetermined distance from the first side edge, wherein the second predetermined distance is greater than the first predetermined distance such that the outer strip is thickened away for the first and second side edges;

an inner strip positioned against the outer strip;

a gas-tight seal joining the outer strip to the inner strip to form an inflatable bladder having two bladder ends, a bladder length between the two ends greater than the circumference of a limb at a selected location, two bladder sides and a bladder midline between the two bladder sides;

wherein at the bladder ends the outer strip has the second thickness at the bladder midline and the first thickness at a location between the bladder midline and a bladder side and wherein the inner strip has side edges and side edge surfaces along each side edge;

the gas-tight seal has an inner perimeter and an outer perimeter, and wherein the inner strip is folded so that the side edge surfaces face toward the bladder midline and are located within the outer perimeter.

13. A low cost tourniquet cuff for stopping blood flow into a patient's limb, comprising:

a first strip having first and second side edges, a midline equidistant from the first and second side edges, and a first side edge surface along the first side edge;

a second strip positioned against the first strip;

a gas-tight seal having an inner perimeter and an outer perimeter and joining the first and second strips to form an inflatable bladder having a length greater than the circumference of a limb at a selected location;

wherein the first strip is folded so that the first side edge surface faces toward the midline and is located within the outer perimeter; wherein the second strip has a first side edge and a first stiffness along the first side edge, and a second stiffness along the strip at a predetermined distance from the first side edge that is greater than the first stiffness;

the inflatable bladder has two ends, a length between the two ends greater than the circumference of a limb at a selected location, two sides and a bladder midline between the two sides; and wherein at the bladder ends the second strip has the second stiffness at the bladder midline and the first stiffness at a location between the bladder midline and a bladder side.

14. The tourniquet cuff of claim 13 wherein the first strip has a top surface, a bottom surface, and a first width;

the second strip has a top surface, a bottom surface positioned against the top surface of the first strip and has a second width narrower than the first width;

the first strip is folded over the second strip so that the top surface of the first strip is in contact with the top surface of the second strip, and the seal joins the top surface of the first strip to the top surface of the second strip.

15. The tourniquet cuff of claim 14 wherein the seal further joins the top surface of the first strip to the bottom surface of the second strip.

16. The tourniquet cuff of claim 13 and including a connector communicating pneumatically with the bladder for releasably connecting the cuff to a tourniquet instrument to establish a gas-tight passageway between the bladder and the instrument, wherein the connector includes identification means for indicating a physical characteristic of the cuff before the gas-tight passageway is pressurized by the tourniquet instrument.

17. A method of making a low cost tourniquet cuff comprising the steps of positioning an inner strip against an outer strip, the outer strip having first and second side edges, a first thickness along the first side edge and a second thickness along the strip at a predetermined distance from the first side edge, the second thickness being greater than the first thickness;

joining the outer and inner strips near the first and second side edges with gas-tight seals, thereby forming the sides of an inflatable bladder with a bladder midline equidistant from the bladder sides; and further joining the outer and inner strips together with gas-tight seals spaced apart by a predetermined length greater than the circumference of a limb at a selected location, thereby forming the ends of the inflatable bladder, wherein at the bladder ends the thickness of the outer strip is greater at the bladder midline than at a bladder side.

* * * * *